US012667697B2

(12) United States Patent
Wang et al.

(10) Patent No.: US 12,667,697 B2
(45) Date of Patent: Jun. 30, 2026

(54) MULTI-DIRECTIONAL ADJUSTABLE SHEATH AND TRANSCATHETER INTERVENTION SYSTEM

(71) Applicant: HANGZHOU VALGEN MEDTECH CO., LTD., Hangzhou (CN)

(72) Inventors: Jianan Wang, Hangzhou (CN); Xianbao Liu, Hangzhou (CN); Zetao Wang, Hangzhou (CN); Weiwei Zhang, Hangzhou (CN); Tingchao Zhang, Hangzhou (CN)

(73) Assignee: Hangzhou Valgen Medtech Co., Ltd., Hangzhou (CN)

( * ) Notice: Subject to any disclaimer, the term of this patent is extended or adjusted under 35 U.S.C. 154(b) by 492 days.

(21) Appl. No.: 18/258,585

(22) PCT Filed: Dec. 15, 2021

(86) PCT No.: PCT/CN2021/138268
§ 371 (c)(1),
(2) Date: Jun. 21, 2023

(87) PCT Pub. No.: WO2022/143169
PCT Pub. Date: Jul. 7, 2022

(65) Prior Publication Data
US 2024/0033482 A1 Feb. 1, 2024

(30) Foreign Application Priority Data

Dec. 29, 2020 (CN) .......................... 202011593342.0
Dec. 29, 2020 (CN) ........................ 202023250781.X

(51) Int. Cl.
*A61M 25/01* (2006.01)
*A61F 2/24* (2006.01)
*A61M 25/00* (2006.01)

(52) U.S. Cl.
CPC ....... *A61M 25/0144* (2013.01); *A61F 2/2466* (2013.01); *A61M 25/0045* (2013.01);
(Continued)

(58) Field of Classification Search
CPC .... A61F 2/2427; A61F 2/2436; A61F 2/2466; A61M 25/0147; A61M 25/005;
(Continued)

(56) References Cited

U.S. PATENT DOCUMENTS 6,544,215 B1    4/2003  Bencini et al.
7,563,267 B2 *  7/2009  Goldfarb ................ A61B 17/08
                                                           606/151
(Continued)

FOREIGN PATENT DOCUMENTS

CN          103446655  A      12/2013
CN          103706017  A       4/2014
(Continued)

*Primary Examiner* — Tuan V Nguyen
(74) *Attorney, Agent, or Firm* — Sand, Sebolt & Wernow Co., LPA

(57) ABSTRACT

Disclosed are a sheath adjustable in multiple directions and a transcatheter interventional system. The sheath that can be adjusted in multiple directions includes: a body section, a bending section, connected with the distal end of the body section, the bending section is a multi-layer composite tube body and includes a plurality of segments, the middle layer of the multi-layer composite tube body is a woven mesh, and the density of the woven mesh of the plurality of segments is gradually reduced in the direction from the proximal end to the distal end; and at least a pair of traction mechanisms, each pair of the traction mechanism respectively passes through the bending section and the body section, to adjust the bending angle of the bending section to different directions.

20 Claims, 7 Drawing Sheets

(52) U.S. Cl.
CPC .... *A61M 25/0147* (2013.01); *A61M 25/0152* (2013.01); *A61M 2025/0161* (2013.01); *A61M 2205/0216* (2013.01)

(58) Field of Classification Search
CPC ........... A61M 25/015; A61M 25/0144; A61M 25/0152; A61M 25/053; A61M 25/0045; A61M 25/0082; A61M 25/0012; A61M 2025/015; A61M 2025/0161
See application file for complete search history.

(56) References Cited

U.S. PATENT DOCUMENTS

| | | | | |
|---|---|---|---|---|
| 2005/0137622 | A1* | 6/2005 | Griffin | A61B 17/12136 |
| | | | | 606/198 |
| 2010/0314031 | A1* | 12/2010 | Heideman | A61M 25/0012 |
| | | | | 156/149 |
| 2012/0197193 | A1* | 8/2012 | Krolik | A61B 5/6853 |
| | | | | 604/99.04 |
| 2019/0321171 | A1* | 10/2019 | Morriss | A61F 2/2436 |
| 2020/0155798 | A1* | 5/2020 | Yang | A61N 1/057 |

FOREIGN PATENT DOCUMENTS

| | | | |
|---|---|---|---|
| CN | 105311730 | A | 2/2016 |
| CN | 209679245 | U | 11/2019 |
| CN | 211935126 | U | 11/2020 |
| CN | 113413244 | A | 9/2021 |
| CN | 215130890 | U | 12/2021 |

* cited by examiner 12000                                                        11000

10000                              20000                    1000

MULTI-DIRECTIONAL ADJUSTABLE SHEATH AND TRANSCATHETER INTERVENTION SYSTEM

CROSS-REFERENCE TO RELATED APPLICATIONS

This disclosure claims the priority of Chinese patent disclosure No. 202011593342.0 filed on Dec. 29, 2020 with the Patent Office of the State Intellectual Property Office of the People's Republic of China, entitled sheath adjustable in multiple directions and transcatheter intervention system, and the priority of Chinese patent disclosure No. 202023250781.X filed on Dec. 29, 2020 with the Patent Office of the State Intellectual Property Office of the People's Republic of China, entitled sheath adjustable in multiple directions and transcatheter intervention system, which are incorporated herein by reference.

FIELD

The present disclosure relates to the field of medical devices, and in particular, relates to a sheath adjustable in multiple directions and a transcatheter intervention system.

BACKGROUND

The mitral valve is a one-way valve between the left atrium and left ventricle of the heart. A normal, healthy mitral valve can control the flow of blood from the left atrium to the left ventricle, while preventing blood from flowing from the left ventricle to the left atrium. The mitral valve includes a pair of leaflets, called anterior and posterior leaflets. When the edges of the anterior and posterior leaflets coaptate, the mitral valve closes completely, preventing blood from flowing from the left ventricle to the left atrium. When the leaflets of the mitral valve or related structures thereof are qualitatively or functionally altered, the anterior and posterior leaflets of the mitral valve are misaligned, thus, when the left ventricle of the heart contracts, the mitral valve cannot fully close, causing blood to flow back from the left ventricle to the left atrium, resulting a series of patho-physiological changes known as mitral regurgitation. The same is true for tricuspid regurgitation.

Transcatheter valve intervention technology refers to delivering various valve repair devices to the mitral valve or tricuspid valve through a catheter with a smaller diameter, and repairing the diseased mitral valve or tricuspid valve by remote operation outside the patient's body, thereby treating mitral or tricuspid regurgitation.

SUMMARY

A first aspect of the present disclosure provides a sheath adjustable in multiple directions, comprising:
  a body section;
  a bending section connected with a distal end of the body section; and
  at least one pair of traction mechanisms;
  wherein the bending section is a multi-layer composite tube body and comprises a plurality of segments, a middle layer of the multi-layer composite tube body is a woven mesh, and a density of the woven mesh of the plurality of segments gradually decreases in a direction from a proximal end to a distal end, each pair of traction mechanisms respectively passes through the bending section and the body section in turn to adjust bending angles of the bending section in different directions.

In some embodiments, an outer layer of the multi-layer composite tube body is an elastomer, and a hardness of the elastomer of the plurality of segments gradually decreases along the direction from the proximal end to the distal end.

In some embodiments, the bending section comprises a first segment, a second segment and a third segment in sequence along the direction from the proximal end to the distal end, preferably, a density of the woven mesh of the first segment is in a range of 45-60 PPI, a density of the woven mesh of the second segment is in a range of 35-45 PPI, and a density of the woven mesh of the third segment is in a range of 20-35 PPI.

In some embodiments, a hardness of the elastomer of the first segment ranges from 30 to 50D, preferably, a hardness of the elastomer of the second segment ranges from 50 to 65D, and a hardness of the elastomer of the third segment ranges from 65 to 80D.

In some embodiments, the traction mechanism comprises: an anchoring ring and a traction wire, the anchoring ring is sleeved on the distal end of the woven mesh, the distal end of the traction wire is connected with the anchoring ring, and the proximal end of the traction wire extends along an axial direction of the woven mesh.

In some embodiments, at least a pair of wire threading holes are axially penetrated through a distal end surface of the anchoring ring, after the traction wire is folded in half, each end portion respectively passes through one of the wire threading holes and extends in the axial direction of the woven mesh.

In some embodiments, the traction wire is embedded on an outer wall surface or the inner wall surface of the woven mesh.

In some embodiments, a reinforcing wire is wound around the outside of the traction wire, and an outer surface of the reinforcing wire is fixedly connected with the elastomer.

In some embodiments, the woven mesh is woven from a plurality of metal wires, preferably a wire diameter of the reinforcing wire is substantially the same as a wire diameter of the metal wire, and a winding pitch of the reinforcing wire is greater than an interval between two adjacent metal wires in the woven mesh.

In some embodiments, the bending section is pre-bent and shaped.

In some embodiments, the bending section comprises: a bending portion, a first curved portion, a transition portion, and a second curved portion connected sequentially along the direction from the distal end to the proximal end, the second curved portion is not coplanar with the body section, and is communicated with the body section with a first preset angle.

In some embodiments, an angle between the projection of the body section in X-plane and the projection of the second curved portion in X-plane is in a range of 20° to 50°, and an angle between the projection of the body section in Z-plane and the projection of the second curved portion in Z-plane is in a range of 0° to 20°.

In some embodiments, the second curved portion is not coplanar with the transition portion and is communicated with the transition portion at a second preset angle.

In some embodiments, an angle between the projection of the second curved portion in X-plane and the projection of the transition portion in X-plane is in a range of 20° to 50°, and an angle between the projection of the second curved portion in Z-plane and the projection of the transition portion in Z-plane is in a range of 0° to 20°.

In some embodiments, the transition portion is not coplanar with the first curved portion, and is communicated with the first curved portion at a third preset angle.

In some embodiments, an angle between the projection of the transition portion in X-plane and the projection of the first curved portion in X-plane is in a range of 0° to 35°, and an angle between the projection of the transition portion in Y-plane and the projection of the first curved portion in Y-plane is in a range of 0° to 15°.

In some embodiments, the first curved portion is not coplanar with the bending portion, and communicated with the bending portion at a fourth preset angle.

In some embodiments, an angle between the projection of the first curved portion in X-plane and the projection of the bending portion in X-plane is in a range of 0° to 35°, and an angle between the projection of the first curved portion in Y-plane and the projection of the bending portion in Y-plane is in a range of 0° to 15°.

In some embodiments, the body section is a multi-lumen tube, the positions of the plurality of lumens of the multi-lumen tube correspond to the positions of the wire threading holes, and an end of the traction wire extends inside the corresponding lumen of the multi-lumen tube after passing through the wire threading hole.

In some embodiments, the bending section comprises at least one developing unit.

In some embodiments, wherein the bending section comprises three developing units, one of the developing units is arranged at the distal end of the anchoring ring, and the other two are arranged in the transition portion at intervals.

A second aspect of the present disclosure provides a transcatheter access system, comprising a guide sheath and a sheath adjustable in multiple directions as described above.

In some embodiments, the present disclosure provides a sheath adjustable in multiple directions and a transcatheter access system, the sheath adjustable in multiple directions comprises: a body section; a bending section connected with a distal end of the body section and being a multi-layer composite tube body and comprises a plurality of segments, the middle layer of the multi-layer composite tube body being a woven mesh, and the density of the woven mesh of the multiple sections decreasing gradually along the direction from the proximal end to the distal end; at least one pair of traction mechanisms, each pair of the traction mechanisms respectively passing through the bending section and the body section in turn, so as to adjust the bending of the bending section to different directions angle; the present disclosure sets the density of the woven mesh at the distal end of the bending section to minimum, so that the traction mechanism can be controlled by small forces, and the distal end of the sheath can be quickly adjusted to suit the delivery path or the treatment site, so as to improve the bending performance of the bending section. The density of the woven mesh at the proximal end of the bending section is set to maximum, ensuring that the proximal end of the bending section is not easily bent, so as to provide stable support for the delivery and bending of the sheath.

BRIEF DESCRIPTION OF THE DRAWINGS

The accompanying drawings, which are incorporated in and constitute a part of this specification, illustrate embodiments consistent with the disclosure and together with the description serve to explain the principles of the disclosure.

In order to illustrate the technical solutions in the embodiments of the present disclosure more clearly, the accompanying drawings required for the description of the embodiments will be briefly introduced below. It is obvious that for ordinary technicians in the art, other drawings can be obtained according to these drawings without paying creative labor.

DETAILED DESCRIPTION

Figure 1:
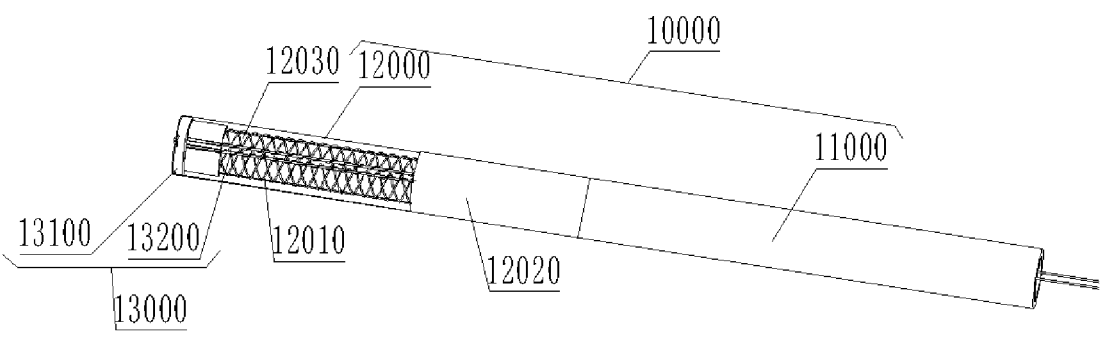
FIG. 1 is a schematic structural diagram of the sheath in the first embodiment.

In order to make the purpose, technical solutions, and advantages of the present disclosure more clear, the technical solutions in the embodiments of the present disclosure will be described clearly and completely below with reference to the accompanying drawings in the embodiments of the present disclosure. Obviously, the described embodiments are the some, but not all, of the embodiments. Based on the embodiments in the present disclosure, all other embodiments obtained by those of ordinary skilled in the art without creative work fall within the protection scope of the present disclosure.

It should be understood that the orientation or positional relationship indicated by "front", "rear", "up", "down", "left", "right", "vertical", "horizontal", "vertical", "horizontal", "top", "bottom", "inner", "outer", "head", "tail", etc. is based on the orientation or positional relationship shown in the drawings, constructed and operated in a specific orientation, only for facilitating the description of the technical solution, not indicating that the device or element referred to must have a specific orientation, and therefore cannot be construed as a limitation of the present disclosure.

It should also be noted that, unless otherwise expressly specified and limited, terms such as "install", "connect", "connection", "fix" and "set" should be understood in a broad sense, for example, it may be a fixed connection, or a detachable connection or integral; it can be directly connected or indirectly connected through an intermediate medium, and it can be the internal communication of two elements or the interaction relationship between the two elements. When an element is referred to as being "on" or "under" another element, it can be "directly" or "indirectly" on the other element, or one or more intervening elements may also be present. For those of ordinary skilled in the art, the specific meanings of the above terms in the present disclosure can be understood according to specific situations.

In the description of the present disclosure, it should be noted that the proximal end refers to the end of the instrument or component close to the operator, the distal end refers to the end of the instrument or component away from the operator; the axial direction refers to the direction parallel to the line connecting the center of the distal end and the proximal end of the instrument or component, the radial direction refers to the direction perpendicular to the axial direction, and the circumferential direction refers to the direction surrounding the axial direction.

First Embodiment

Referring to FIGS. 1 to 5, the present disclosure provides a sheath adjustable in multiple directions for providing a delivery path for an interventional medical device.

The sheath adjustable in multiple directions in the first embodiment comprises a body section 11000 and a bending section 12000. A proximal end of the body section 11000 is connected with a handle for supporting the sheath 10000; the bending section 12000 is connected with the distal end of the body section 11000. The bending section 12000 is a multi-layer composite tube body, specially including: an inner layer 12030, a middle layer 12010, and an outer layer 12020 sequentially sheathed and welded together from inside to outside. During manufacture, the inner layer 12030 is firstly sleeved on a lining rod, then the middle layer 12010 and the outer layer 12020 are sleeved in sequence, and finally the outer layer 12020 is melted to fully fuse with the inner layer 12030 and the middle layer 12010 to form into an integral piece. Wherein, the inner layer 12030 is provided as a polytetrafluoroethylene film to ensure that the inner wall is smooth, which is beneficial to the passage of medical devices such as guide wires or valve repair devices.

Figure 2:
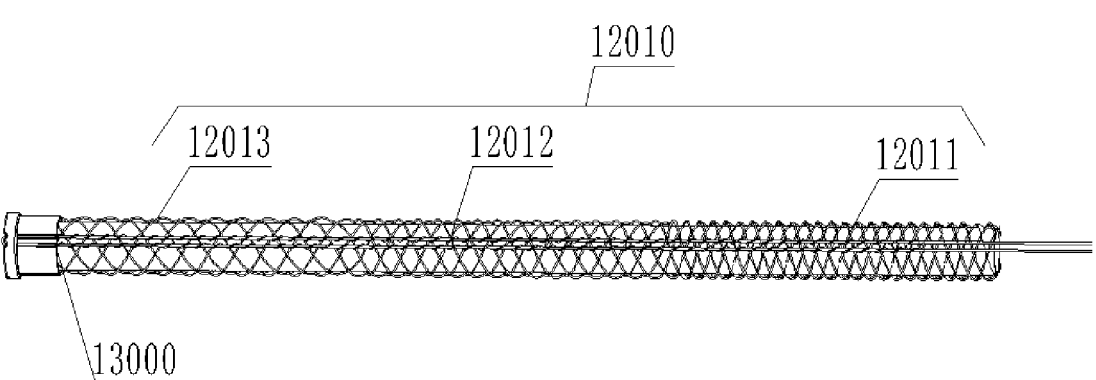
FIG. 2 is a schematic structural diagram of the bending section in the first embodiment.

As shown in FIG. 2, the middle layer 12010 is a spring tube or woven mesh made of metal material, preferably a woven mesh. Exemplarily, the woven mesh can be formed by weaving, winding, etc., using circular or flat metal wires such as stainless steel wires or tungsten wires, wherein the wire diameter of the metal wires ranges from about 0.03 to 0.30 mm. In this embodiment, the middle layer 12010 is a woven mesh woven from flat stainless steel wires of about 0.05×0.15 mm.

Referring to FIG. 2, the bending section 12000 includes a plurality of segments, and the density of the woven mesh of the plurality of segments gradually decreases along the direction from the proximal end to the distal end. In some embodiments, the woven mesh comprises a first woven mesh 12011, a second woven mesh 12012, and a third woven mesh 12013 in sequence along a proximal-to-distal direction. In some embodiments, the density of the first woven mesh 12011 ranges from about 45 PPI to 60 PPI, the density of the second woven mesh 12012 ranges from about 35 PPI to 45 PPI, and the density of the third woven mesh 12013 ranges from about 20 PPI to 35 PPI, thus the sheath 10000 can not only meet the support function of the proximal end, but also does not affect the bending function of the distal end of the sheath, ensuring the support and reducing the force value required for bending, thereby the safety of the device is effectively guaranteed.

Figure 3:
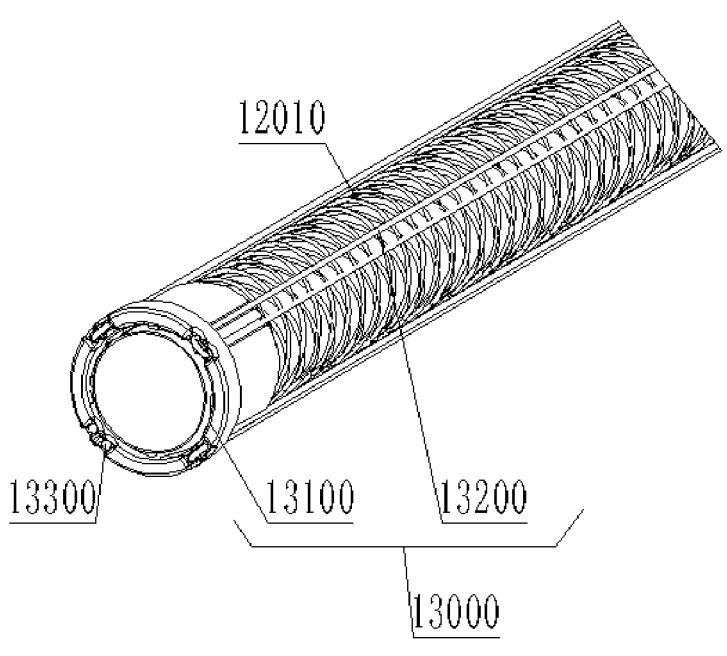
FIG. 3 is a schematic structural diagram of the cooperation between the traction wire and the woven mesh in the first embodiment.

The bending section 12000 further includes at least a pair of traction mechanisms 13000, each pair of traction mechanisms 13000 respectively passes through the bending section 12000 and the body section 11000 in sequence to adjust the bending angles of the bending section 12000 in different directions. In some embodiments, the traction mechanisms 13000 are provided in multiple pairs, and each pair of traction mechanisms 13000 adjusts the bending angle of the bending section 12000 in one direction, and so on. The specific logarithm of the traction mechanism 13000 can be increased or decreased as required. In theory, the greater the pairs of the traction mechanism 13000, the greater the bending angle of the bending section 12000. Referring to FIG. 3, in this embodiment, the traction mechanisms 13000 are provided in four pairs, and the four pairs of traction mechanisms 13000 are distributed at equal intervals in the circumferential direction of the bending section 12000 to realize the bending angle of the bending section 12000 in at least four directions.

The density of the woven mesh of the distal end of the bending section 12000 is smaller, and the density of the woven mesh of the proximal end is greater, so that the traction mechanism 13000 can be controlled by small forces, and the bending performance of the bending section 12000 can be effectively improved, thereby the distal end of the sheath 10000 can be quickly adjusted to the bending angle suitable for the delivery path or the treatment site, so as to deliver the distal end of the sheath 10000 to the vicinity of the mitral valve 20000, while ensuring that the proximal end of the bending section 12000 is not easily bent. Thus, a stable support function is provided for the delivery and bending of the sheath 10000.

In order to further facilitate the deformation of the bending section 12000 to achieve rapid bending, referring to FIG. 1, the outer layer 12020 of the bending section 12000 is configured as an elastomer, and the hardness of the elastomer of the plurality of sections gradually decreases along the direction from the proximal end to the distal end, thereby ensuring that the proximal end of the bending section 12000 further provides a stable support for the delivery and bending of the sheath 10000, and the bending performance of the distal end of the bending section 12000 is further effectively improved. In some embodiments, the outer layer 12020 is made of a thermoplastic, which may be composed of nylon, polyamide, block polyamide, polyurethane, etc. alone, or a copolymer of these thermoplastics. The elastomer of the outer layer of the first woven mesh has a hardness in the range of about 30 to 50D, the elastomer of the outer layer of the second woven mesh has a hardness in the range of about 50 to 65D, and the elastomer of the outer layer of the third woven mesh has a hardness in the range of about 65 to 80D. In this embodiment, the hardness of the elastomer of the outer layer 12020 sleeved on the outside of the first woven mesh 12011 is 35D, the hardness of the elastomer of the outer layer 12020 sleeved on the outside of the second woven mesh 12012 is 55D, and the hardness of the elastomer of the outer layer 12020 sleeved outside the third woven mesh 12013 is 72D.

Referring to FIG. 3, the traction mechanism 13000 includes: an anchoring ring 13100 and a traction wire 13200, the anchoring ring 13100 is sleeved on the distal end of the woven mesh, the distal end of the traction wire 13200 is connected with the anchoring ring 13100, and the proximal end of the traction wire 13200 extends along the axial direction of the woven mesh until it is connected with a bend regulating mechanism on the handle, so that the operator can pull the bend regulating mechanism at the proximal end to drive the bending section 12000 connected with the anchoring ring 13100 to bend in the direction of traction. In some embodiments, at least one pair of threading holes 13300 are axially penetrated through the distal end surface of the anchoring ring 13100. In some embodiments, the number of thread holes 13300 corresponds to the number of traction wires 13200 on a one-to-one basis.

After the traction wire 13200 is folded in half, each end correspondingly passes through the wire threading hole 13300 and extends along the axial direction of the woven mesh, wherein the anchoring ring 13100 can be made of stainless steel, tungsten, platinum-iridium and other metals, or alloy tube body with a thickness of about 0.15 to 1.00 mm, and the wire threading hole 13300 can be arranged as a circle, a square, a polygon or other special shapes. In some embodiments, the traction wire 13200 may be a round or flat metal wire having a diameter of about 0.05 to mm, in some embodiments, a stainless steel wire, or a tungsten wire. The form of the traction wire 13200 can be a single metal wire or a multi-strand wire formed by winding a plurality of metal wires. In the embodiment, the traction wire 13200 is made of multiple strands of stainless steel wire by winding.

In some embodiments, referring to FIG. 3, each pair of threading holes 13300 includes at least two adjacently disposed threading holes 13300, the traction wire 13200 is U-shaped and includes axially parallel aligned a first segment and a second segment, and a bending portion connected between the first segment and the second segment. The first and second segments of each traction wire 13200 are distributed parallelly on the side walls of the woven mesh, respectively, and the bending portion passes through a pair of wire holes 13300 on the distal surface of the anchoring ring 13100 and spans between the connection of two adjacent wire holes 13300. Due to the relatively greater force area during traction, this connection avoids stress concentration and ensures connection strength and stability. Each group of traction wires 13200 is connected with a corresponding pair of wire threading holes 13300, which are distributed on the sides of the woven mesh. In some embodiments, four sets of traction wires 13200 positioned adjacently are adopted.

Of course, the connection between the traction wire 13200 and the anchoring ring 13100 can also be the following ways: the traction wire 13200 is folded and bypasses the threading hole 13300 of the anchoring ring 13100 and then reversely looped back to the anchoring ring 13100; or the traction wire 13200 connects with the anchor ring 13100 through thread hole 13300.

In some embodiments, in order to ensure that the bending direction of the bending section 12000 is consistent with the direction of the acting force, the body section 11000 is a multi-lumen tube. In some embodiments, the multi-lumen tube is made of a polymer material with higher hardness. Exemplarily, the multi-lumen tube can be directly extruded from materials such as nylon, block polyether, polycarbonate, etc. It can be formed by hot melting. The lumen of the multi-lumen tube corresponds to the position of the threading hole 13300. In some embodiments, the first and second segments of each traction wire 13200 passes through the anchoring ring 13100 and then enters into the lumen of the multi-lumen tube correspondingly, so that the first and second segments extend along the tube wall of the woven mesh parallelly to the proximal end of the body section 11000, so as to ensure that the force experienced by the proximal end of the body section 11000 can all act on the anchoring ring 13100, and finally ensure the bending direction of the bending section 12000 is consistent with the direction of the applied force.

Figure 4:
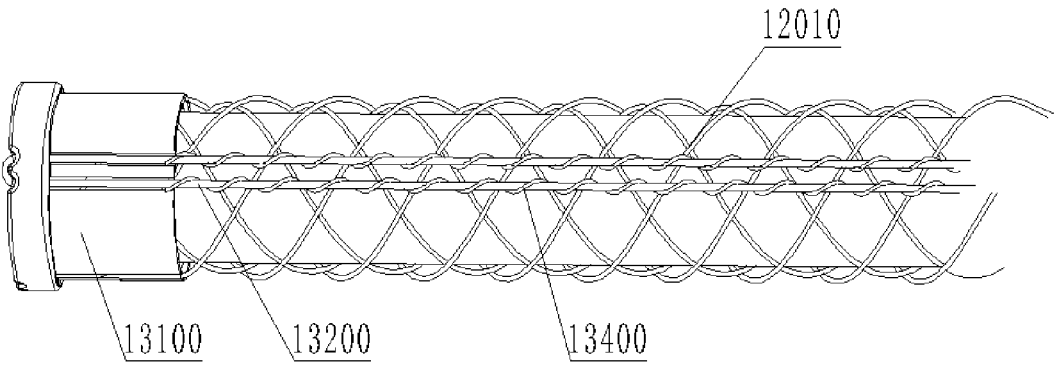
FIG. 4 is a schematic structural diagram of the cooperation between the reinforcing wire and the traction wire in the first embodiment.

Referring to FIGS. 3 and 4, the proximal end of the traction wire 13200 is embedded on the outer wall of the woven mesh, the outer surface of the traction wire 13200 is wound with a reinforcing wire 13400, and the outer wall of the reinforcing wire 13400 is fixedly connected with the elastomer. In some embodiments, the reinforcing wire 13400 is heat-fused integrally with the elastomer to form a passageway for the traction wire 13200. Therefore, after the traction wire 13200 is subjected to a pulling force, the pulling force received by the traction wire 13200 acts on the reinforcing wire 13400, and since the reinforcing wire 13400 is fixedly connected with the elastomer, it is ensured that the surrounding reinforcing wire 13400 won't escape from the elastomer, thereby effectively avoiding the failure of the device. Meanwhile, under the support force of the woven mesh, even after the bending angle of the sheath 10000 exceeds 90 degrees, the traction wire 13200 can still be adjusted to bend without buckling. Wherein, the reinforcing wire 13400 is generally made of metal wire, exemplarily stainless steel wire or tungsten wire, etc. In this embodiment, stainless steel wire is preferred. It can be understood that, in other embodiments, the first and second segments of the traction wire 13200 can also be surrounded by other tubes that can provide lumen channels and can be bent without buckling, for example, tubes made of materials such as tetrafluoroethylene or polyurethane elastomers.

Figure 5:
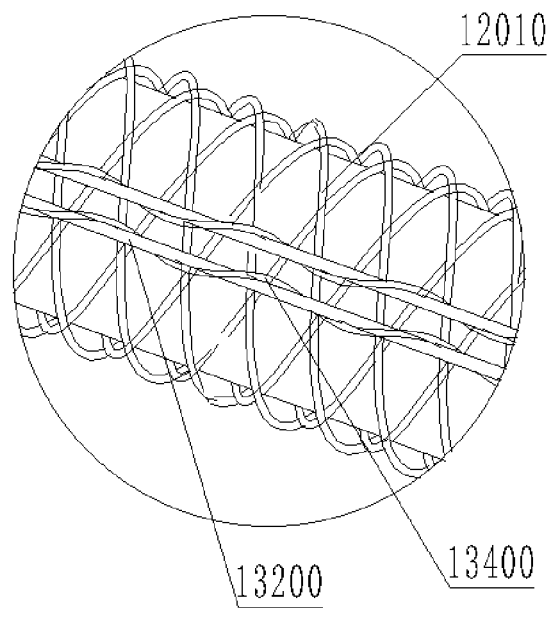
FIG. 5 is a comparison diagram of the winding pitch of the reinforcing wire in the first embodiment and the pitch of two adjacent metal wires in the woven mesh.

Referring to FIG. 5, the wire diameter of the reinforcing wire 13400 is equal to the wire diameter of the metal wire for weaving the woven mesh, and the winding pitch of the reinforcing wire 13400 is greater than the distance between two adjacent metal wires of the woven mesh. The design of this embodiment can effectively avoid that during the bending process of the sheath 10000, as the pitch between the wound reinforcing wires 13400 is too small, the reinforcing wires 13400 touch each other before the metal wires of the woven mesh does, thereby affecting the influence of the bending function of the sheath 10000.

In order to facilitate the observation of the position of the bending section 12000, the bending section 12000 comprises at least one developing unit, wherein the developing unit is made of a radiopaque material, exemplarily, a developing ring, a developing point, or other forms. In this embodiment, the developing unit adopts a developing ring, which is made of metals or alloys such as tantalum, tungsten, platinum-iridium, etc., and has a thickness ranging from about 0.05 to 0.50 mm.

The proximal end of the sheath that can be bent in multiple directions is also provided with a handle connected with the body section 11000 of the sheath that can be bent in multiple directions. A bend regulating mechanism is provided on the handle, and the proximal end of the traction wire 13200 is fixed on the bend regulating mechanism of the handle.

During operation, the operator pulls different bend regulating mechanisms at the proximal end, so that the bending section 12000 connected with the anchoring ring 13100 can be driven to bend in different pulling directions under the action of different traction wires 13200.

Figure 14:
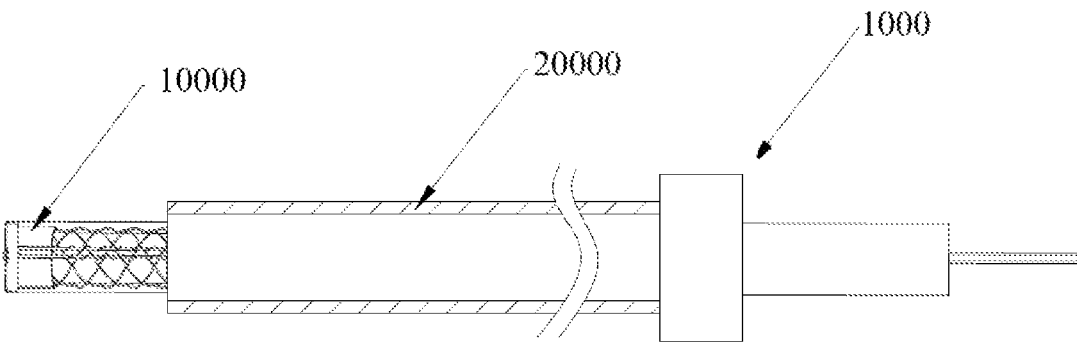
FIG. 14 is a schematic structural diagram of the transcatheter intervention system in the present disclosure.

Referring to FIG. 14, the present disclosure also provides a transcatheter intervention system 1000, comprising a guide sheath 20000 and the aforementioned sheath 10000 adjustable in multiple directions. The guide sheath 20000 is a pre-shaped catheter or an adjustable catheter, sheath 10000 adjustable in multiple directions, and movably extends through the guide sheath 20000, and the distal end of the sheath 10000 adjustable in multiple directions protrudes from the distal end of the guide sheath 20000. Therefore, the cooperating of the guide sheath 20000 and the sheath 10000 adjustable in multiple directions can adapt to more complex physiological and anatomical structure, and is more conducive to the realization of transcatheter interventional therapy.

Second Embodiment

Figure 6:
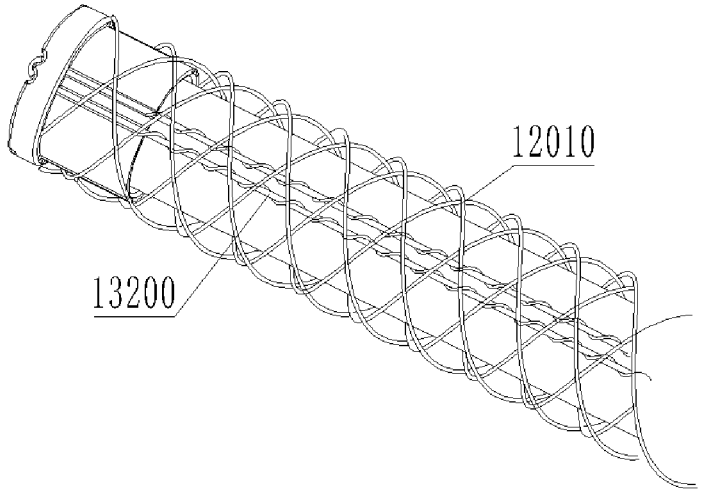
FIG. 6 is a schematic structural diagram of the cooperation between the traction wire and the woven mesh in the second embodiment.

Referring to FIG. 6, compared with the sheath adjustable in multiple directions in the first embodiment, the difference is that the proximal end of the traction wire 13200 is embedded on the inner wall surface of the woven mesh.

In some embodiments, the traction wire 13200 is distributed on the inner wall of the woven mesh and extends along the axial direction of the sheath 10000. When the traction wire 13200 is subjected to a pulling force, the woven mesh will provide a supporting force to the traction wire 13200, so that the traction wire 13200 will not be separated from the outer layer 12020, ensuring that the device is not easy to fail during using.

In addition, in this embodiment, when the traction wire 13200 is subjected to a traction force, the woven mesh can provide a support force for the traction wire 13200, thus there is no need to provide a reinforcing wire 13400 surrounding the traction wire 13200, thereby reducing the difficulty of producing the device and production costs.

Third Embodiment

Referring to FIGS. 7 to 12, compared with the sheath adjustable in multiple directions in the first embodiment, the difference is that the bending section 12000 is pre-bent and shaped, and the shape thereof is that the proximal end of the bending section 12000 points to the atrial septum 30000, the distal end of the bending section 12000 points to the mitral valve 20000. Therefore, the transcatheter intervention system of this embodiment is especially suitable for transcatheter mitral valve repair therapy.

In this embodiment, the bending section 12000 is pre-bent and shaped in a natural state, and is designed to have a shape with a certain spatial solid angle, which can quickly realize a valve repair device such as a valve clamp to across the atrial septum 30000, and points to the vicinity of the mitral valve 20000 from the left atrium, so that only a slight adjustment of the sheath 10000 is required to adjust the bending portion 12100 to the position facing the mitral valve 20000. Therefore, it can be more convenient to adjust the valve repairing device towards the mitral valve 20000, reducing the operation time, and reducing the difficulty of the operation.

Figure 7:
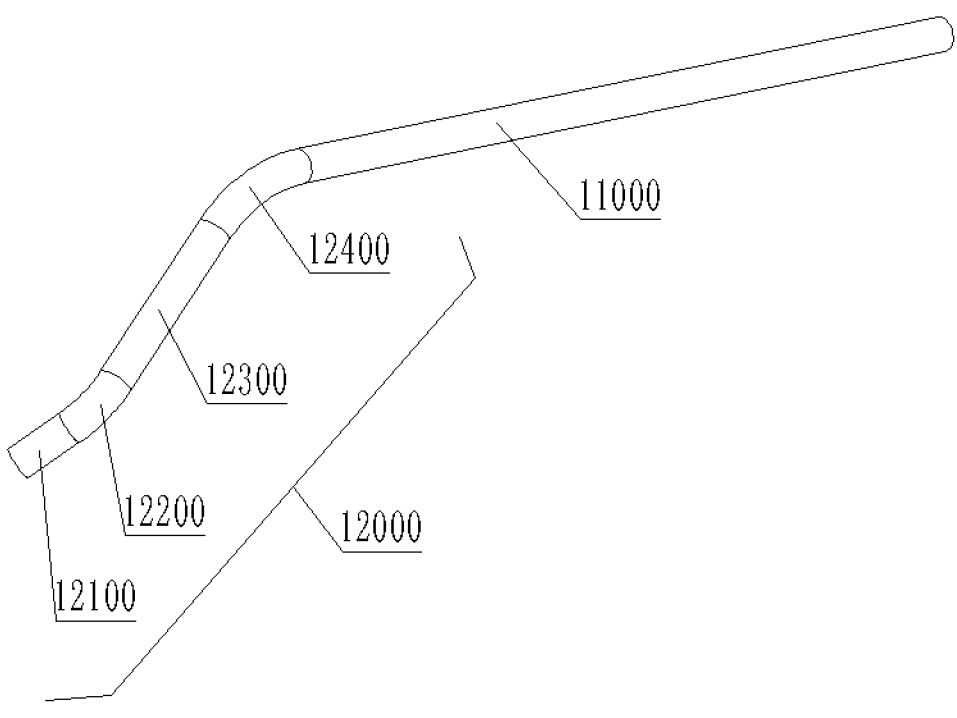
FIG. 7 is a schematic structural diagram of the sheath in the third embodiment.
Figure 8:
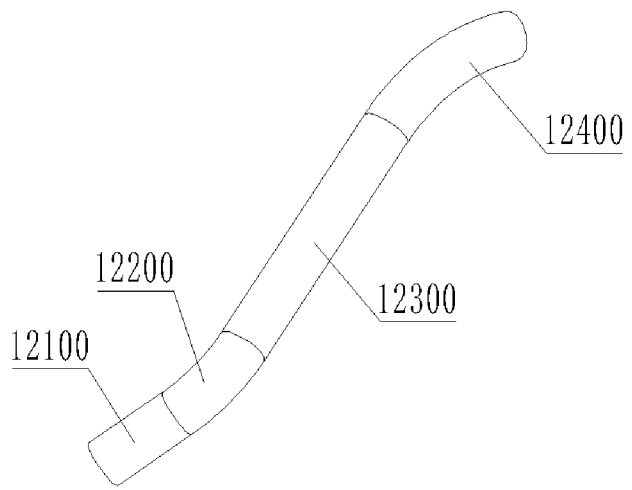
FIG. 8 is a schematic structural diagram of the bending section in the third embodiment.
Figure 9:
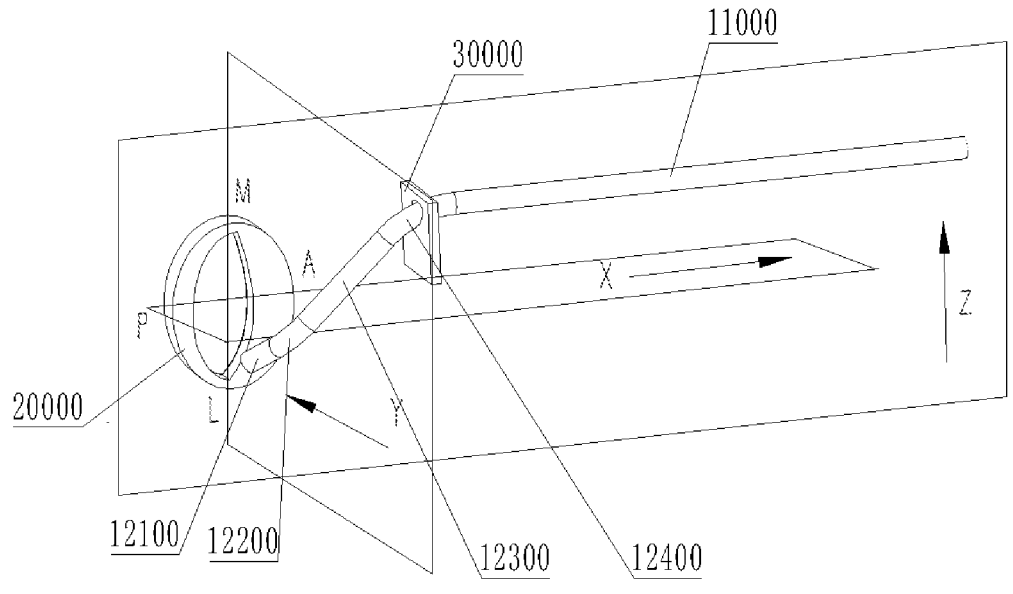
FIG. 9 is a diagram showing the using state of the sheath in cooperation respectively with the atrial septum and the mitral valve in the third embodiment.

Referring to FIGS. 7 to 9, the bending section 12000 comprises: a bending portion 12100, a first curved portion 12200, a transition portion 12300, and a second curved portion 12400 connected with each other sequentially along the direction from the distal end to the proximal end.

The second curved portion 12400 is not coplanar with the body section 11000 and communicates with each other at a first preset angle. In some embodiments, the angle between the projection of the body section 11000 in the X-plane and the projection of the second curved portion 12400 in X-plane is about 20° to 50°, the angle between the projection of the body section 11000 in the Z-plane and the projection of the second curved portion 12400 in Z-plane is about 0° to 20°.

The second curved portion 12400 is not coplanar with the transition portion 12300 and is communicated with each other at a second preset angle. In some embodiments, the angle between the projection of the second curved portion 12400 in the X-plane and the projection of the transition portion 12300 in X-plane is about 20° to 50°, the angle between the projection of the second curved portion 12400 in the Z-plane and the projection of the transition portion 12300 in Z-plane is about 0° to 20°.

The transition portion 12300 is not coplanar with the first curved portion 12200 and is communicated with each other at a third preset angle. In some embodiments, the angle between the projection of the transition portion 12300 in the X-plane and the projection of the first curved portion 12200 in X-plane is about 0° to 35°, the angle between the projection of the transition portion 12300 in the Y-plane and the projection of the first curved portion 12200 in Y-plane is about 0° to 15°.

The first curved portion 12200 is not coplanar with the curved portion 12100 and is communicated with each other at to a fourth preset angle. In some embodiments, the angle between the projection of the first curved portion 12200 in the X-plane and the projection of the bending portion 12100 in X-plane is about 0° to 35°, the angle between the projection of the first curved portion 12200 in the Y-plane and the projection of the bending portion 12100 in Y-plane is about 0° to 15°.

Therefore, after the sheath 10000 in this embodiment is delivered from the inferior vena cava to the right atrium, when the bending portion 12100, the first bending portion 12200 and the transition portion 12300 are delivered to the atrial septum 30000 in sequence, under the action of the first curved portion 12200, the curved section 12100 is bent to substantially point toward the mitral valve 20000. Under the action of the second curved portion 12400, the transition portion 12300 is substantially directed toward the atrial septum 30000, that is, referring to FIG. 9, the second curved portion 12400 points to the interatrial septum 30000, the transition portion 12300 crosses the interatrial septum 30000, and the first curved portion 12200 makes the bending portion 12100 to point toward the mitral valve 20000. Thus, the above design only needs slight fine adjustment to adjust the bending section to point to the mitral valve 20000, so that the valve repairing device can be more conveniently adjusted to point to the mitral valve 20000, reducing the operation time and operation difficulty.

In order to better indicate the different positions of the bending section 12000 in the human body, in this embodiment, three developing units are provided, wherein: one developing unit is provided at the distal end of the anchoring ring 13100 to indicate the most distal position; the other two developing units are provided spaced apart at the transition portion 12300 to indicate spanning the interatrial septum 30000; the distance between the two developing units ranges from about 4 to 10 mm. In some embodiments, the distance between the two developing units is about 6.5 mm.

Figure 10:
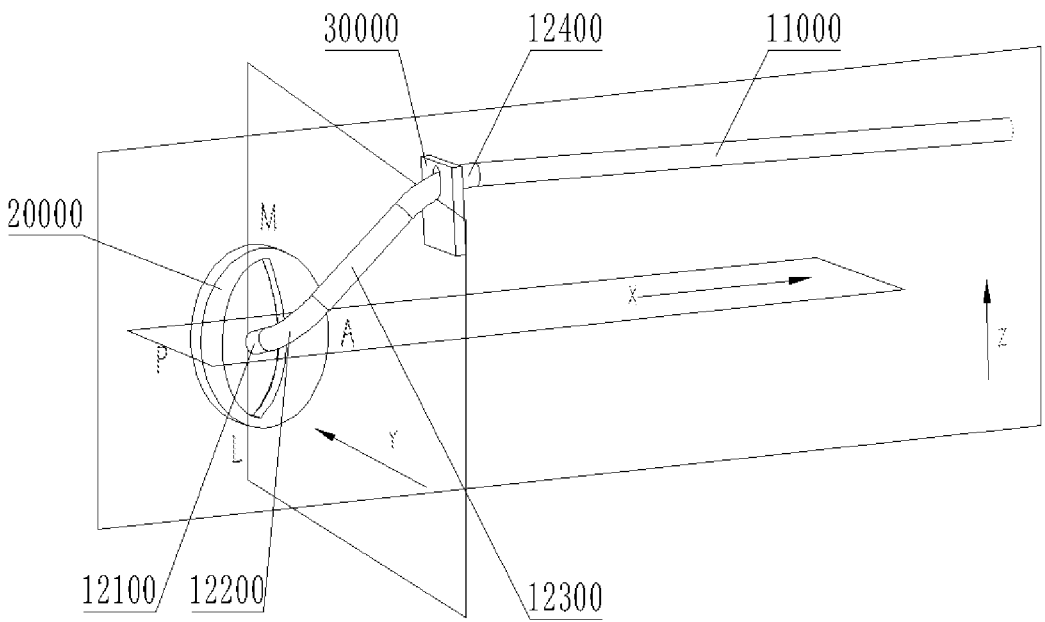
FIG. 10 is a diagram of a using state after the bending section is adjusted toward the M direction in the third embodiment.
Figure 11:
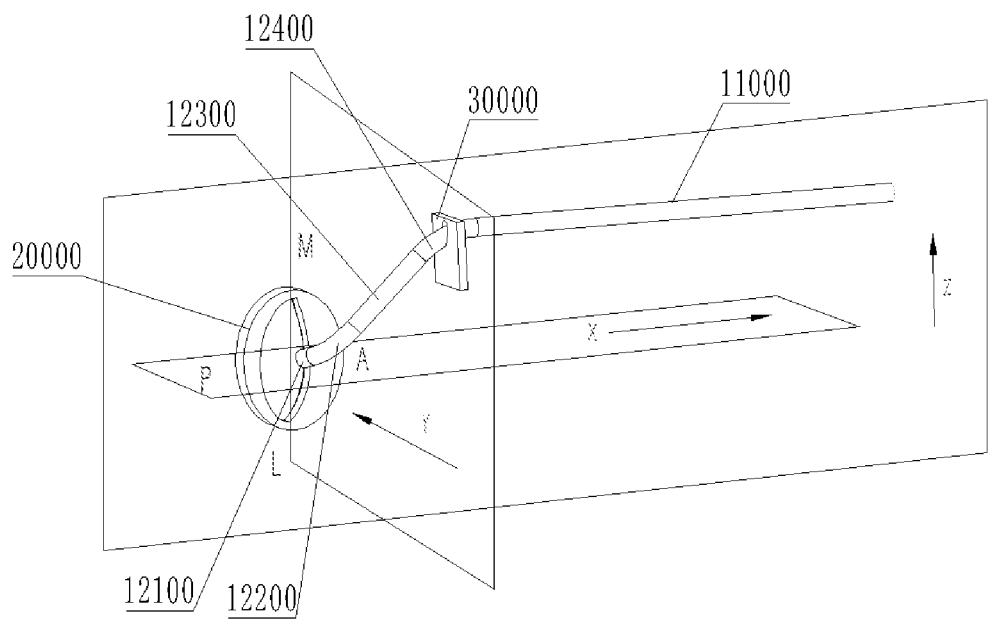
FIG. 11 is a diagram of a using state after the bending section is adjusted toward the A direction in the third embodiment.
Figure 12:
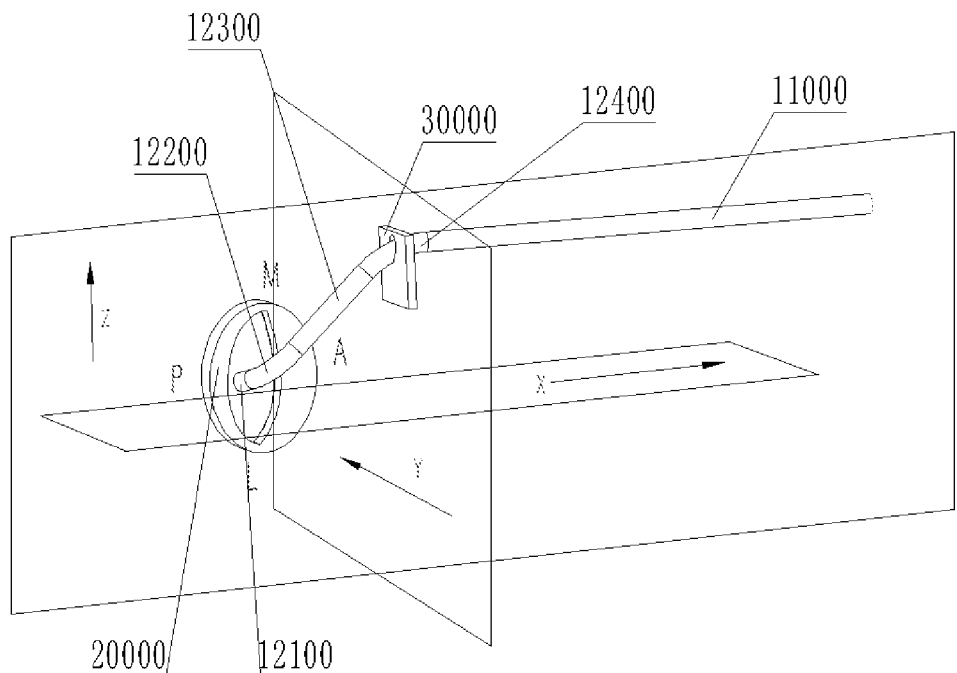
FIG. 12 is a diagram of a using state after the bending section is adjusted toward the P direction in the third embodiment.

Referring to FIGS. 9 to 12, the use process of the sheath adjustable in multiple directions of the present embodiment is as follows:

Referring to FIG. 9, firstly, the sheath 10000 is transported to the left atrium along the inferior vena cava, and positioned via the imaging ring on the sheath 10000 by means of medical imaging equipment such as CT, ultrasound or angiography, so as to place the transition portion 12300 in the interatrial septum 30000, since the bending section 12000 is pre-bent and shaped, the bending portion 12100 faces towards the L junction position of the mitral valve 20000;

Then, by observing the delivery path in real time, the bending angle of the sheath 10000 is adjusted in real time: exemplarily, refer to FIG. 10, if the distal end of the sheath 10000 needs to be adjusted to be close to the M junction position, it is necessary to apply a traction force in the M direction to the traction wire 13200 to drive the bending portion 12100 to bend in the M direction, so as to bend the distal end of the sheath 10000 to a position close to the M junction; similarly, referring to FIG. 11, if it is necessary to bend the distal end of the sheath 10000 to the position close to the A junction position, a traction force in the A direction is applied to the traction wire 13200 to drive the bending portion 12100 to bend in the direction A, so as to bend the sheath 10000 to the position close to the junction A; referring to FIG. 12, if it is necessary to bend the distal end of sheath 10000 to the position close to the junction position of P, a traction force in the P direction is applied to the traction wire 13200 to drive the bending portion 12100 to bend in the direction P, so as to bend the sheath 10000 to the position close to the junction of P. To sum up, in this embodiment, only slight fine adjustment of the sheath 10000 is required to bend the curved portion 12100 to the position facing the mitral valve 20000. Therefore, it can be more convenient to adjust the valve repairing device towards the mitral valve 20000, reducing the operation time and the difficulty of the operation.

Fourth Embodiment

Figure 13:
FIG. 13 is a schematic structural diagram of the sheath in a fourth embodiment.

Referring to FIG. 13, compared with the sheath adjustable in multiple directions in the first embodiment, the difference is that the body section 11000 is a multi-layer composite tube body and integrally formed with the bending section 12000.

In this embodiment, the structure of the body section 11000 is not a single multi-lumen tube, but adopts the same design as the structure of the bending section 12000, that is, the body section 11000 is also provided as a multi-layer composite tube body. During the production process, it can be directly integrally hot-melted with the bending section 12000 without additional secondary connection processing, thereby effectively simplifying the process and production steps, effectively improving efficiency, and reducing production costs.

What is claimed is:

1. A sheath adjustable in multiple directions, comprising:
a body section;
a bending section connected with a distal end of the body section; and
at least one pair of traction mechanisms;
wherein the bending section is a multi-layer composite tube body and comprises a plurality of segments, a middle layer of the multi-layer composite tube body is a woven mesh, and a density of the woven mesh of the plurality of segments gradually decreases in a direction from a proximal end to a distal end thereof, each pair of traction mechanisms respectively passes through the bending section and the body section in turn to adjust bending angles of the bending section in different directions;
wherein the traction mechanism comprises:
an anchoring ring and a traction wire, wherein the anchoring ring is sleeved on the distal end of the woven mesh, the distal end of the traction wire extends along an axial direction of the woven mesh, a reinforcing wire is wound around the outside of the traction wire.

2. The sheath of claim 1, wherein an outer layer of the multi-layer composite tube body is an elastomer, and a hardness of the elastomer of the plurality of segments gradually decreases along the direction from the proximal end to the distal end.

3. The sheath of claim 2, wherein the bending section comprises a first segment, a second segment and a third segment in sequence along the direction from the proximal end to the distal end, a density of the woven mesh of the first segment is in a range of 45-60 PPI, a density of the woven mesh of the second segment is in a range of 35-45 PPI, and a density of the woven mesh of the third segment is in a range of 20-35 PPI.

4. The sheath of claim 3, wherein a hardness of the elastomer of the first segment ranges from 30 to 50D, a hardness of the elastomer of the second segment ranges from 50 to 65D, and a hardness of the elastomer of the third segment ranges from 65 to 80D.

5. The sheath of claim 2, wherein
the outer surface of the reinforcing wire is fixedly connected with the elastomer.

6. The sheath of claim 1, wherein at least a pair of wire threading holes are axially penetrated through a distal end surface of the anchoring ring, after the traction wire is folded in half, each end portion respectively passes through one of the threading holes and extends in the axial direction of the woven mesh.

7. The sheath of claim 6, wherein the traction wire is embedded on an outer wall surface or the inner wall surface of the woven mesh.

8. The sheath of claim 7, wherein the woven mesh is woven from a plurality of metal wires, a wire diameter of the reinforcing wire is substantially as the same as a wire diameter of the metal wire, and a winding pitch of the reinforcing wires is greater than an interval between two adjacent metal wires in the woven mesh.

9. The sheath of claim 6, wherein the body section is a multi-lumen tube, the positions of the plurality of lumens of the multi-lumen tube correspond the positions of the wire threading holes, and an end of the traction wire extends into the corresponding lumens of the multi-lumen tube after passing through the wire threading hole.

10. The sheath of claim 1, wherein the bending section is pre-bent and shaped.

11. The sheath of claim 10, wherein the bending section comprises: a bending portion, a first curved portion, a transition portion, and a second curved portion connected sequentially along the direction from the distal end to the proximal end, the second curved portion is not coplanar with the body section, and is communicated with the body section with a first preset angle.

12. The sheath of claim 11, wherein an angle between the projection of the body section in X-plane and the projection of the second curved portion in X-plane is in a range of 20° to 50°, and an angle between the projection of the body section in Z-plane and the projection of the second curved portion in Z-plane is in a range of 0° to 20°, so that the second curved portion is communicated with the body section at the first preset angle.

13. The sheath of claim 11, wherein the second curved portion is not coplanar with the transition portion, and is communicated with the transition portion at a second preset angle.

14. The sheath of claim 13, wherein an angle between the projection of the second curved portion in X-plane and the projection of the transition portion in X-plane is in a range of 20° to 50°, and an angle between the projection of the second curved portion in Z-plane and the projection of the transition portion in Z-plane is in a range of 0° to 20°, so that the second curved portion is communicated with the transition portion at the second preset angle.

15. The sheath of claim 11, wherein the transition portion is not coplanar with the first curved portion, and is communicated with the first curved portion at a third preset angle.

16. The sheath of claim 15, wherein an angle between the projection of the transition portion in X-plane and the projection of the first curved portion in X-plane is in a range of 0° to 35°, and an angle between the projection of the transition portion in Y-plane and the projection of the first curved portion in Y-plane is in a range of 0° to 15°, so that the transition portion is communicated with the first curved portion at the third preset angle.

17. The sheath of claim 11, wherein the first curved portion is not coplanar with the bending portion, and is communicated with the bending portion at a fourth preset angle.

18. The sheath of claim 17, wherein an angle between the projection of the first curved portion in X-plane and the projection of the bending portion in X-plane is in a range of 0° to 35°, and an angle between the projection of the first curved portion in Y-plane and the projection of the bending portion in Y-plane is in a range of 0° to 15°, so that the first curved portion is communicated with the bending portion at the fourth preset angle.

19. The sheath of claim 11, wherein the bending section comprises three developing units, one of the developing units is arranged at the distal end of the anchoring ring, and the other two are arranged in the transition portion at intervals.

20. A transcatheter intervention system, comprising:
a guide sheath and a sheath adjustable in multiple directions of claim 1, wherein the sheath movably extends through the guide sheath.

* * * * *